US008686197B2

(12) United States Patent
Notheis et al.

(10) Patent No.: US 8,686,197 B2
(45) Date of Patent: Apr. 1, 2014

(54) METHOD FOR IMPROVING THE COLOR NUMBER OF TRIMETHYLOLPROPANE

(75) Inventors: Ulrich Notheis, Dormagen (DE); Hans-Dieter Gerriets, Duisburg (DE); Michael Friederich, Krefeld (DE)

(73) Assignee: LANXESS Deutschland GmbH, Cologne (DE)

( * ) Notice: Subject to any disclaimer, the term of this patent is extended or adjusted under 35 U.S.C. 154(b) by 219 days.

(21) Appl. No.: 13/388,199

(22) PCT Filed: Aug. 6, 2010

(86) PCT No.: PCT/EP2010/061459
§ 371 (c)(1),
(2), (4) Date: Mar. 26, 2012

(87) PCT Pub. No.: WO2011/015644
PCT Pub. Date: Feb. 10, 2011

(65) Prior Publication Data
US 2012/0178973 A1    Jul. 12, 2012

(30) Foreign Application Priority Data

Aug. 7, 2009  (EP) .................................. 09167480

(51) Int. Cl.
*C07C 29/141*  (2006.01)
*C07C 29/74*   (2006.01)

(52) U.S. Cl.
USPC .......................................................... 568/854

(58) Field of Classification Search
USPC .......................................................... 568/854
See application file for complete search history.

(56) References Cited

U.S. PATENT DOCUMENTS

| 2,186,272 A | 1/1940 | Wyler |
| 2,329,515 A | 9/1943 | Cox |
| 3,097,245 A | 7/1963 | Russell et al. |
| 3,379,624 A | 4/1968 | Lindkvist et al. |
| 4,514,578 A | 4/1985 | Immel et al. |
| 5,248,818 A | 9/1993 | Werle et al. |
| 5,603,835 A | 2/1997 | Cheung et al. |
| 6,586,642 B2 | 7/2003 | Dernbach et al. |
| 7,211,701 B2 | 5/2007 | Muller et al. |

FOREIGN PATENT DOCUMENTS

| DE | 4123062 | 1/1993 |
| DE | 4126730 | 2/1993 |
| DE | 10029055 | 1/2002 |

OTHER PUBLICATIONS

European Search Report from co-pending Application EP09167480 dated Jan. 20, 2010, 2 pages.

*Primary Examiner* — Elvis O Price
(74) *Attorney, Agent, or Firm* — Nicanor A. Kohncke

(57) ABSTRACT

The present invention relates to a method for producing trimethylolpropane having a low color number by processing a raw reaction solution obtained according to the inorganic Cannizarro process while adhering to precisely defined pH values.

5 Claims, No Drawings

METHOD FOR IMPROVING THE COLOR NUMBER OF TRIMETHYLOLPROPANE

CROSS REFERENCE TO RELATED PATENT APPLICATIONS

The present patent application claims the right of priority under 35 U.S.C. §119 (a)-(d) and 35 U.S.C. §365 of International Application No. PCT/EP10/061459, filed 6 Aug. 2010, which is entitled to the right of priority of European Patent Application No. 09167480.4 filed on 7 Aug. 2009.

The present invention relates to a process for preparing trimethylolpropane having a low color number by work-up at precisely defined pH values of a crude reaction solution obtained by the inorganic Cannizzaro process.

Trimethylolpropane, hereinafter referred to as TMP, is widely used in industry for producing polyesters, polyurethanes, polyethers, polymer foams, plasticizers, alkyd resins, protective paints, lubricants, textile finishes and elastomers. Furthermore, it replaces glycerol in some industrial applications.

On an industrial scale, TMP is prepared, for example by the Cannizzaro process which comprises an aldol condensation of butanal and formaldehyde in a first step and a cross-Cannizzaro reaction between the aldol condensation product of the first step and formaldehyde in a second step. When the process proceeds with consumption of stoichiometric amounts of an inorganic base such as sodium hydroxide or calcium hydroxide, it is also referred to as an inorganic Cannizzaro process. The dimethylol-butanal formed as aldol condensation product in the first step reacts in the second step with excess formaldehyde in a disproportion reaction to form TMP and, depending on the base used, the corresponding formate, for example sodium formate or calcium formate.

Commercially available TMP grades usually have a coloration which is caused by the presence of impurities. However, in some applications, for example the production of particularly transparent polyesters or particular surface coating raw materials, this coloration interferes. A variety of different work-up methods by means of which an improvement in the color number of TMP is said to be achieved are described in the literature.

The work-up of TMP-containing reaction mixtures as can be obtained by the Cannizzaro process generally comprises neutralization of the residual base remaining in the reaction mixture. This neutralization is typically followed by concentration steps and the removal of inorganic coproducts and organic secondary products, with the latter frequently being separated off by distillation.

U.S. Pat. No. 3,097,245 describes a process for preparing TMP having an APHA color number in the range from 50 to 200. This color number is achieved by adherence to particular reaction conditions in the Cannizzaro reaction in respect of temperature, reaction time, pH and concentration of the starting compounds. Furthermore, the reaction is followed by treatment of the crude TMP solution obtained with an ion-exchange resin.

U.S. Pat. No. 5,603,835 discloses a process for preparing TMP having APHA color numbers of less than 100 by extractive after-treatment of crude TMP solutions with an ether or an ester.

The two above-described methods of improving the color number of TMP have the disadvantage that they are technically complicated since particular conditions have to be adhered to precisely and, in addition, they require the use of an ion-exchange resin or the introduction of at least one solvent.

SU-A 125552 describes a hydrogenation for purifying TMP which has been prepared by the Cannizzaro process. Hydrogenation over nickel, zinc, molybdenum or copper catalysts gives TMP having a content of about 98% after distillation. It is stated that the TMP obtained is colorless, but no color number is reported. However, it has been found in practice that the color number which can be obtained by this method is not satisfactory for many purposes.

A further method of improving the color number of TMP by hydrogenation is described in the patent application DE 199 63 442 A. Here, TMP is purified by distillation after it has been produced and is subsequently preferably treated with a heterogeneous catalyst under hydrogen pressure. The color number achieved by hydrogenation can be improved further by prior multiple distillation.

However, all hydrogenation processes for improving the color number have the disadvantages of a high outlay for apparatus and a reduction in the quality of the TMP obtained due to catalyst abrasion. The costs for the catalyst also reduce the economic efficiency.

DE 100 29 055 A describes a process for improving the color number of TMP, in which the TMP which has been prepurified by distillation and has a purity of preferably >95% is subjected to heat treatment, preferably at temperatures of from 160 to 240° C., and the TMP is subsequently purified again, preferably by distillation. The heat treatment step converts the color-imparting secondary components into higher-boiling, relatively nonvolatile components. However, a disadvantage of this process is that the heat treatment has to be followed by another purification step, for example a distillation, or this purification step has to be coupled with the heat treatment in order to remove these higher-boiling secondary components and obtain a TMP having a low color number.

DE1493048 B describes a work-up by means of a thin film evaporator by means of which the crude TMP is distilled. The crude TMP is firstly neutralized, then centrifuged and passed through a rapid evaporator and subsequently brought to a pH of about 4-8, preferably 5-6, before the final purification. The color number of the TMP obtained can attain 0 APHA. A disadvantage of this process is that acid has to be added at two places in the process. Which acid is used for neutralization and setting the pH is not indicated. DE 10164264 A describes a process for preparing a TMP having a low APHA number, in which n-butyraldehyde is reacted with formaldehyde in the presence of inorganic base to give TMP-containing reaction mixtures, water and inorganic salts are at least partly removed from these reaction mixtures and the crude TMP obtained is subjected to at least partial removal of high boilers and low boilers separated by distillation into one or more low boiler fractions, one or more middle fractions containing predominantly TMP and one or more high boiler and/or low boiler fractions.

The examples of DE 10164264 A indicate that the reaction mixture is set to pH 6 by means of formic acid after the condensation reaction, but the neutralization is not discussed and not related to the color number. The reaction mixture is subsequently concentrated, calcium formate is filtered off, the mixture is concentrated further and the crude TMP mixture then obtained is distilled by means of a thin film evaporator. The overhead product from the thin film evaporator has a content of 94.9% and an APHA color number of 148 and is brought to a purity of 99.4% or 99.1% and an APHA color number of 13 or 8 in further distillation steps. In the comparative example, a purity of 99.3% and an APHA color number of 22 are obtained. Although this process gives TMP having a good color number, it has the advantage that high reflux ratios of 48 are employed in the distillation in order to achieve this color number.

There was therefore still the object of providing an efficient process for preparing TMP having a low color number, which overcomes the disadvantages of the prior art.

We have now found a process for preparing TMP having a low color number by reaction of butyraldehyde with formaldehyde in the presence of an inorganic base to give a TMP-containing reaction mixture and subsequent work-up of the TMP-containing reaction mixture, which is characterized in that the work-up of the TMP-containing reaction mixture comprises setting the pH of the TMP-containing reaction mixture to a value of from 4.50 to 5.90 based on a temperature of 50° C., where the setting of the pH is preferably carried out using an organic carboxylic acid.

The scope of the invention encompasses all desired and possible combinations of components, value ranges and process parameters indicated below, either generally or in preferred ranges.

The molar ratio of formaldehyde to butyraldehyde in the reaction is, for example, from 2.5 to 6.0, preferably from 3.0 to 5.0, particularly preferably from 3.0 to 4.0 and very particularly preferably from 3.1 to 3.5:

The molar ratio of base equivalents from the inorganic bases to butyraldehyde in the reaction is, for example, from 0.8 to 2.5, preferably from 1.0 to 2.0, particularly preferably from 1.0 to 1.4 and very particularly preferably from 1.05 to 1.2.

As inorganic bases, preference is given to using hydroxides or carbonates of alkali metals or alkaline earth metals, particularly preferably sodium hydroxide and calcium hydroxide, with calcium hydroxide being even more preferred. When calcium hydroxide is used, this can, for example, be used as technical-grade product having a purity of greater than 80%, preferably 90%, particularly preferably 95%.

The molar ratio of calcium hydroxide to butyraldehyde can accordingly be, for example, from 0.4 to 1.25, preferably from 0.5 to 1.0, particularly preferably from 0.5 to 0.7 and very particularly preferably from 0.525 to 0.6.

Formaldehyde is preferably used as aqueous solution having a content of from 10 to 50% by weight. In a preferred variant, formaldehyde having a content of from 25 to 40% by weight is used. Additional water can be added to the reaction mixture, which improves the selectivity of the reaction but increases the outlay in the work-up because of the greater amounts of water.

Furthermore, at least one compound which is able to avoid or at least suppress formose reactions can be added in the reaction. Suitable compounds are known to those skilled in the art and are described, for example, in U.S. Pat. Nos. 2,186,272, 2,329,515, EP 510 375 A, DE A 41 23 062 and DE A 41 26 730. They encompass, for example, metal salts of copper, iron, manganese, chromium, nickel, cobalt, silver, platinum, lead, molybdenum, tungsten, bismuth, vanadium, zirconium, titanium, niobium, hafnium, optionally in combination with sparging with air or oxygen or boron compounds. Preference is given to iron salts such as iron(II) sulfate and its hydrates and also iron(III) sulfate and its hydrates. The amount of the compounds used can be, for example, from 50 to 1000 ppm based on the total amount of the reaction mixture.

To carry out the reaction, preference is given to initially placing at least part of the formaldehyde and the inorganic base in a reaction vessel and adding butyraldehyde and optionally part of the formaldehyde over a period of from 3 to 180 minutes, preferably from 15 to 120 minutes, particularly preferably from 20 to 60 minutes.

The temperature in the reaction can be, for example, from 20 to 90° C., preferably from 20 to 60° C.

In a preferred variant, the temperature is allowed to rise in a controlled manner during the addition of butyraldehyde, for example essentially linearly from 20 to 60° C.

After the addition is complete, the mixture is stirred further at the final temperature for, for example, from 5 to 180 minutes, preferably from 30 to 90 minutes.

In another preferred mode of operation, the reaction is carried out continuously, for example in a tube reactor, a cascade of vessels or a plate heat exchanger.

The TMP-containing reaction mixtures obtained after the reaction typically have a pH in the range from 9.0 to 11.0.

The TMP-containing reaction mixtures obtained are then set to a pH of from 4.50 to 5.90, preferably from 4.50 to 5.60 and particularly preferably from 5.00 to 5.60, and very particularly preferably from 5.25 to 5.45, based on a temperature of 50° C., with the adjustment preferably being carried out using an organic carboxylic acid.

Suitable organic carboxylic acids encompass monocarboxylic acids such as formic acid, acetic acid and n-butanoic acid; dicarboxylic acids such as oxalic acid, malonic acid and maleic acid and also tricarboxylic acids such as citric acid. Preferred organic carboxylic acids are monocarboxylic acids, with formic acid being very particularly preferred.

Surprisingly, the color number of the TMP can be influenced in a simple way via the pH set in the subsequent work-up. What happens is then the color number typically becomes smaller, the lower the pH in the range mentioned.

However, secondary reactions such as the formation of TMP formate can occur at the low pH values as a function of the temperature and the residence time in the further work-up, ultimately reducing the yields of TMP. Furthermore, an excessively low pH leads to decomposition of residual formaldehyde in the crude TMP and thus to foaming in the first distillation, which prevents stable operation of the plant.

It is easy for a person skilled in the art to determine the pH in the neutralization at which an excellent color number together with a high yield can be achieved by means of a preliminary experiment as a function of the parameters which would be selected for the preceding reaction.

The further work-up following the setting of the pH can be carried out in a manner known per se. The work-up can be carried out batchwise or continuously, with a continuous further work-up being preferred.

In a preferred embodiment of the process of the invention, the further work-up following the setting of the pH according to the invention comprises at least the steps:

a) removal of part of the water and optionally formaldehyde from the TMP-containing, adjusted reaction mixture,
b) separation of calcium formate from the TMP-containing, adjusted reaction mixture to give a TMP-containing crude solution,
c) separation of high boilers from the TMP-containing crude solution to give a crude TMP,
d) distillation of the crude TMP obtained according to step c) to give TMP having a low color number.

In a preferred embodiment, the pH of the TMP-containing reaction mixture is consequently set to a value of from 4.50 to 5.90, based on a temperature of 50° C., after the reaction of butyraldehyde with formaldehyde in the presence of an inorganic base to give a TMP-containing reaction mixture without carrying out one of the steps a) to d) beforehand.

In a further preferred embodiment, the further work-up following the setting of the pH according to the invention comprises the steps a) to d) in the stated order:

Step a) is preferably carried out by distillation, for example in a multistage mode of operation at different pressure levels. Apart from water, excess formaldehyde is usually also at least partly removed here. During the course of the removal of water, inorganic formates can precipitate, particularly when calcium hydroxide is used as base, and these are separated off in step b).

Step b) can be carried out, for example, by filtration, sedimentation and decantation or centrifugation, preferably by filtration or centrifugation.

The temperature in the separation can be, for example, from 20 to 90° C., preferably from 50 to 90° C.

Steps a) and b) can optionally be repeated one or more times.

Step c) is preferably carried out by distillation. In a preferred embodiment, the distillation is carried out by means of thin film evaporators or short path evaporators or other suitable apparatuses which make a short residence time possible. In step c), high boilers are separated off from the crude TMP solution obtained according to step b), with, for the present purposes, high boilers being compounds which boil at a higher temperature than TMP or have no appreciable vapor pressure. Examples of high boilers are diTMP and bisTMP formal and also higher oligomers and formals of TMP.

Crude TMP having a purity of more than 90% by weight is typically obtained in step c).

In step d), the crude TMP obtained according to step c) is purified further by distillation. This can, in a preferred embodiment, be effected by low boilers firstly being separated off from the TMP in a first column. In this context, low boilers are compounds having a lower boiling point than TMP, for example 2-hydroxymethyl-1-butanol, 1-methoxy-2,2-di(hydroxymethyDbutane and 1-[(methoxy)methyloxy]-2,2-di(hydroxymethypbutane. TMP is obtained at the bottom of this column and is subsequently distilled overhead in a further column. Step d) can also be carried out in a single distillation step using thermally coupled columns. Known alternatives are side offtake columns with or without dividing devices, e.g. a dividing wall, from which the pure TMP can be taken off as side stream.

In an alternative embodiment, steps c) and d) can also be carried out simultaneously in one distillation, with the apparatuses described for step c) being able to be used in the same way.

TMP having a low color number and high purity is obtained in the manner described according to the invention.

EXAMPLES

General:

The APHA color numbers [classification of the color according to the platinum-cobalt scale, cf. DIN ISO 6271] were determined using a Lico 300 photometer from Dr. Lange. For this purpose, from 4 to 5 g of TMP were placed in an 11 mm round cell, the round cell was closed by means of a silicone stopper, the TMP was melted at 100° C. and measured. Two measurements were carried out for each sample and the values were averaged.

Example 1

Influence of the Setting of the pH on the Color Number of the Crude Product after Removal of High Boilers Batchwise, 3.15 molar equivalents of 32% strength by weight formaldehyde were diluted with water and admixed at room temperature with 0.56 molar equivalents of calcium hydroxide. 1.00 molar equivalent of butyraldehyde was allowed to run into the vessel over a period of 50 minutes, resulting in the mixture warming to 50° C. The amount of butyraldehyde was 10% by weight based on the total mass, and the final concentration of trimethylolpropane was from 15 to 15.3% by weight. After the reaction, the mixture was stirred at 50° C. for another 40 minutes and the pH was set to the values indicated in the table by means of formic acid. The reaction mixture was subsequently concentrated continuously in a three-stage evaporator at temperatures of from 50 to 80° C. and pressures of from 130 to 260 mbar to a residual water content of from 30 to 33% by weight. Precipitated calcium formate was then separated off at from 75 to 80° C. and the residual water content was reduced to 1.5% by weight at from 80 to 100 mbar and 100° C. The precipitated solids, predominantly calcium formate, were separated off by means of a decanter and the crude TMP was freed of residual low boilers at 10 mbar and from 140 to 150° C. The crude TMP which had been freed of low boilers was distilled overhead in a short path evaporator at 3 mbar and from 130 to 140° C. until 60% had been evaporated. The bottom product from the short path evaporator was concentrated further in three parallel thin film evaporators (TFEs) at from 5 to 10 mbar and a temperature of 170° C. at the top so as to give a bottom product containing less than 10% by weight of residual TMP.

The crude distillates were combined and freed of low boilers in a first column at a temperature at the bottom of 230° C., a temperature at the top of 154° C. and a pressure at the top of 30 mbar. The bottom product from these columns was distilled overhead in a further column at a temperature at the bottom of 220° C. and a temperature at the top of 136° C. at 12 mbar and then had a TMP content of >99% by weight.

Samples of the crude TMP after the thin film evaporators and the final product after the second distillation column were taken and the APHA color number was determined.

| pH in the reaction | APHA of overhead product TFE 1 | APHA of overhead product TFE 2 | APHA of overhead product TFE 3 | APHA of overhead product from second column |
|---|---|---|---|---|
| 5.25 | 110 | 120 | 150 | 7 |
| 5.30 | 130 | 150 | 190 | 9 |
| 5.45 | 170 | 180 | 260 | 13 |
| 5.50 | 200 | 200 | | 15 |

The examples show that even in the low boiler removal, which is carried out by means of a thin film evaporator having only one separation stage, a clearly low-color crude product is obtained at a lower pH. The APHA color number of the TMP after the last distillation before packing was determined taking into account the residence time. The TMP in all cases had a purity in the range from 99.4% to 99.8% by weight.

The experiments show that even small decreases in the pH result in significant improvements in the color number.

What is claimed is:

1. A process for preparing TMP by reaction of butyraldehyde with formaldehyde in the presence of an inorganic base to give a TMP-containing reaction mixture and subsequent work-up of the TMP-containing reaction mixture, characterized in that the work-up comprises setting the pH of the TMP-containing reaction mixture by means of formic acid to a value of from 5.25 to 5.45 based on a temperature of 50° C.

2. The process as claimed in claim 1, characterized in that hydroxides or carbonates of alkali metals or alkaline earth metals are used as inorganic bases.

3. The process as claimed in claim 2, characterized in that the work-up further comprises at least the following steps:
 a) removal of water and optionally formaldehyde from the TMP-containing, adjusted reaction mixture,
 b) separation of solid constituents from the TMP-containing, adjusted reaction mixture to give a TMP-containing crude solution,
 c) separation of high boilers from the TMP-containing crude solution to give a crude TMP,
 d) distillation of the crude TMP obtained according to step c) to give TMP having a low color number.

4. The process as claimed in claim 3, characterized in that steps a) and b) are repeated at least once.

5. The process as claimed in claim 4, characterized in that step c) and d) are carried out simultaneously.

* * * * *